US00PP08934P

United States Patent [19]

Danziger

[11] Patent Number: Plant 8,934

[45] Date of Patent: Oct. 11, 1994

[54] PETUNIA PLANT NAMED CAS 42

[75] Inventor: Gabriel Danziger, Post Beit Dagan, Israel

[73] Assignee: Florfis AG, Binningen, Switzerland

[21] Appl. No.: 162,360

[22] Filed: Dec. 7, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A new and distinct cultivar of petunia plant named Cas 42, characterized by the combined features of large, light pink-violet flowers with light yellow-green throat and weak veining, vigorous growth habit, comparatively large, light green foliage, and semi-erect plant habit later becoming overhanging.

2 Drawing Sheets

The present invention comprises a new and distinct cultivar of petunia, hereinafter referred to by the cultivar name Cas 42.

Cas 42 was originated from a hybridization made by the inventor Gabriel Danziger in a controlled breeding program in Moshav Mishmar Hashiva, Israel in 1992. The female parent was a seedling designated X 81. The male parent of Cas 42 was a seedling designated Y 32. Both parents are proprietary cultivars used in the breeding program.

Cas 42 was discovered and selected as one flowering plant within the progeny of the stated cross by Gabriel Danziger in 1992 in a controlled environment in Moshav Mishmar Hashiva, Israel.

The first act of asexual reproduction of Cas 42 was accomplished when vegetative cuttings were taken from the initial selection in December 1992 in a controlled environment in Moshav Mishmar Hashiva, Israel, by, or under the supervision of, Gabriel Danziger.

Horticultural examination of selected units initiated in December 1992 and continuing thereafter has demonstrated that the combination of characteristics are herein disclosed for Cas 42 are firmly fixed and are retained through successive generations of asexual reproduction.

Cas 42 has not been observed under all possible environmental conditions. The phenotype may vary significantly with variations in environment such as temperature, light intensity and day length, without, however, any variations in genotype.

The following observations, measurements, and comparisons describe plants grown in Hillscheid, Germany, under greenhouse conditions which approximate those generally used in commercial practice.

The following traits have been repeatedly observed and are determined to be basic characteristics of Cas 42, which in combination distinguish this petunia as a new and distinct cultivar:

1. Large, light pink-violet flowers.
2. Light yellow-green throat and weak veining.
3. Vigorous bushy growth habit with branches extending in all directions from center of plant.
4. Semi-erect initial plant habit, later becoming overhanging.
5. Comparatively large, light green foliage.

The accompanying photographic drawings show typical flower and foliage characteristics of Cas 42, with colors being as true as possible with illustrations of this type. The photograph on Sheet 1 illustrates the Cas 42 cultivated in a hanging basket. The photo on Sheet 2 comprises an enlarged showing of single flowers of the new cultivar.

In the following description, color references are made to the Royal Horticultural Society Color Chart. The color values were determined indoors in August. Flowers were taken from plants cultivated in hanging baskets in an open greenhouse in Hillscheid, Germany. For the description, the upper parts of the plants were observed or measured.

Classification:

*Botanical.*—A hybrid of the genus Petunia.

*Commercial.*—Petunia cv Cas 42.

INFLORESCENCE

Plant:

*Growth habit.*—Vigorous, but comparatively compact.

*Plant length.*—80 cm, measured from the base of the stems in the middle of the hanging basket to the tips of the hanging branches (28 week old plants).

*Blooming period.*—Comparatively late; begins 11 weeks after propagation of unrooted cuttings, continually flowering thereafter.

Stem:

*Thickness.*—Young branches, 3 mm; older branches 4 mm.

*Color.*—Light green, approximately 143 C.

*Pubescence.*—Present.

*Branching.*—6–8 branches per week.

*Length of internode.*—15–35 mm.

Leaf:

*Arrangement on stem.*—Opposite, arranged decussately on stem.

*Shape.*—Narrow ovate or elliptic.

*Size (average).*—74 mm long, 37 mm wide, based on largest leaves from a young stem of a plant in flower.

*Thickness.*—Medium.

*Color.*—Light green, between 137 D and 143 C.

*Pubescence.*—Present but weak.

Flower:

*Orientation at opening.*—The bud and peducle form an acute angle with the stem; the open flower and peduncle are oriented approximately at right angles to the stem.

*Type.*—Single.

*Shape.*—Medium to large, with undulating margin.

*Diameter.*—65–70 mm.

*Color.*—Upper (inner) surface at opening: 77 B. Under (outer) surface at opening: 75 D–76 D. Upper (inner) surface at pollen maturity: 75 A. Under (outer) surface at pollen maturity: 75 D–76 C. Throat (inner surface): Light green-yellow. Markings: Weak green veins in the throat, darker speckles (77 B) sometimes visible on the corolla.

*Peduncle length.*—15–25 mm.

*Peduncle color.*—Light green, no anthocyanin.

*Reproductive organs.*—Pistil: 1, green. Stamens: 5, fertile. Anther: white-yellow, with very light brown pollen. Filament: White-green.

Resistance: Very good resistance to rain and good heat tolerance.

It is claimed:

1. A new and distinct cultivar of petunia plant named Cas 42, as illustrated and described.

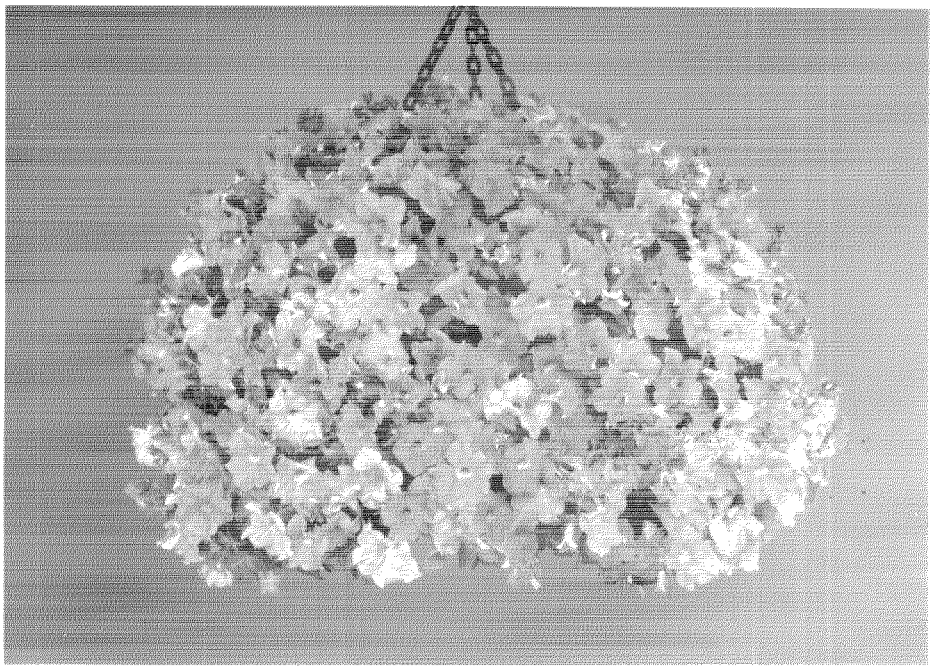

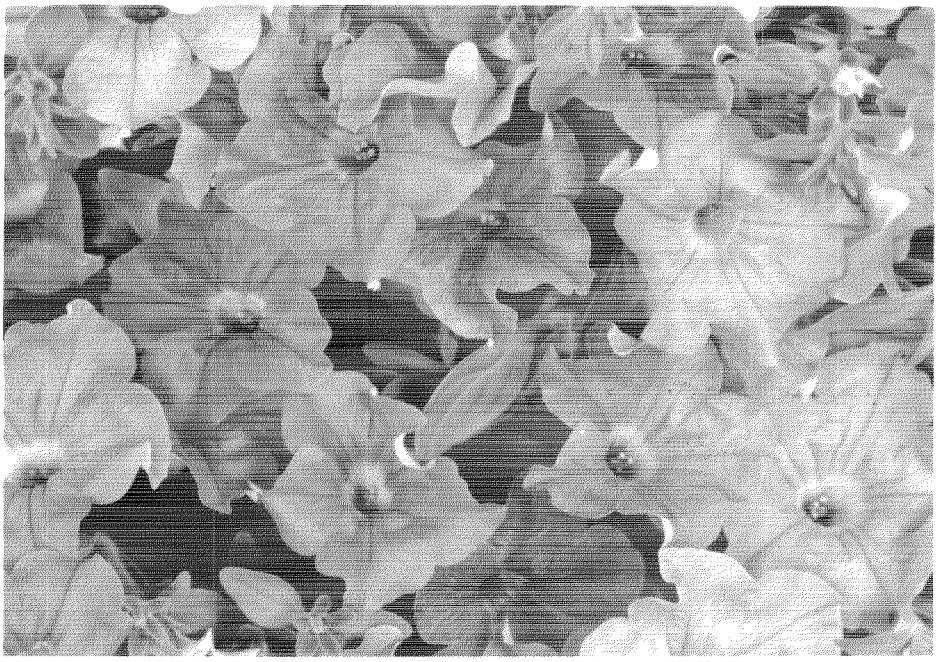

* * * * *